US009364288B2

(12) United States Patent
Smith et al.

(10) Patent No.: US 9,364,288 B2
(45) Date of Patent: Jun. 14, 2016

(54) STERILE BATTERY CONTAINMENT

(75) Inventors: Bret W. Smith, Kings Mills, OH (US);
John A. Hibner, Mason, OH (US);
David N. Plescia, Cincinnati, OH (US);
Foster B. Stulen, Mason, OH (US);
Emmanuel V. Tanghal, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1038 days.

(21) Appl. No.: 13/176,875

(22) Filed: Jul. 6, 2011

(65) Prior Publication Data
US 2013/0009606 A1 Jan. 10, 2013

(51) Int. Cl.
*H02J 7/00* (2006.01)
*H02J 7/14* (2006.01)
*A61B 19/02* (2006.01)
*A61B 17/00* (2006.01)

(52) U.S. Cl.
CPC ......... *A61B 19/0256* (2013.01); *A61B 19/0271* (2013.01); *A61B 2017/00734* (2013.01); *A61B 2019/0201* (2013.01); *A61B 2019/0202* (2013.01); *A61B 2019/0209* (2013.01); *A61B 2019/0267* (2013.01); *A61B 2019/0268* (2013.01); *A61B 2019/0275* (2013.01); *A61B 2019/0278* (2013.01); *A61B 2019/0286* (2013.01)

(58) Field of Classification Search
USPC .......................................... 320/107, 112, 114
See application file for complete search history.

(56) References Cited

U.S. PATENT DOCUMENTS

| 3,894,888 | A  | * | 7/1975  | Gold .............................. 429/110 |
| 4,641,076 | A  | * | 2/1987  | Linden ........................... 320/113 |
| 4,878,493 | A  |   | 11/1989 | Pasternak et al. |
| 6,500,176 | B1 |   | 12/2002 | Truckai et al. |
| 6,520,185 | B1 |   | 2/2003  | Bommannan et al. |
| 6,626,901 | B1 |   | 9/2003  | Treat et al. |
| 6,666,875 | B1 |   | 12/2003 | Sakurai et al. |
| 6,917,183 | B2 |   | 7/2005  | Barlev et al. |
| 7,416,101 | B2 |   | 8/2008  | Shelton, IV et al. |
| 7,738,971 | B2 |   | 6/2010  | Swayze et al. |
| 7,872,446 | B2 |   | 1/2011  | Cover et al. |
| 2002/0025473 | A1 | * | 2/2002  | Peterson ....................... 429/157 |

(Continued)

FOREIGN PATENT DOCUMENTS

| EP | 1 834 568 | 9/2007 |
| WO | WO 2008/033874 | 3/2008 |

(Continued)

OTHER PUBLICATIONS

International Search Report and Written Opinion dated Jan. 18, 2013 for Application No. PCT/US2012/045359.

(Continued)

*Primary Examiner* — Samuel Berhanu

(57) ABSTRACT

An apparatus for delivering electrical power to an electrically powered medical device includes a battery, a first compartment, and a second compartment where the second compartment can hold the first compartment and the first compartment can hold the battery. A sterile space is defined between the first compartment and the second compartment. The first compartment and the battery may be selectively electrically coupled with the electrically powered medical device such that the first compartment does not compromise the sterility of the electrically powered medical device.

17 Claims, 6 Drawing Sheets

(56) References Cited

U.S. PATENT DOCUMENTS

| | | |
|---|---|---|
| 2002/0138090 A1 | 9/2002 | Jewett |
| 2006/0079874 A1 | 4/2006 | Faller et al. |
| 2007/0085496 A1 | 4/2007 | Philipp et al. |
| 2007/0175960 A1 | 8/2007 | Shelton, IV et al. |
| 2007/0182369 A1* | 8/2007 | Gerber et al. ............... 320/112 |
| 2007/0191713 A1 | 8/2007 | Eichmann et al. |
| 2007/0282333 A1 | 12/2007 | Fortson et al. |
| 2008/0057470 A1 | 3/2008 | Levy et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1* | 10/2008 | Zemlok et al. ............... 600/106 |
| 2009/0057369 A1 | 3/2009 | Smith et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209990 A1 | 8/2009 | Yates et al. |
| 2009/0292305 A1* | 11/2009 | Kahler et al. ............... 606/176 |
| 2010/0174415 A1 | 7/2010 | Humayun et al. |
| 2011/0057608 A1 | 3/2011 | Smith et al. |
| 2012/0115007 A1* | 5/2012 | Felder et al. ............... 429/121 |

FOREIGN PATENT DOCUMENTS

| | | |
|---|---|---|
| WO | WO 2009/046394 | 4/2009 |
| WO | WO 2009/070780 | 6/2009 |
| WO | WO 2009/073608 | 6/2009 |

OTHER PUBLICATIONS

U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
"System 6 Aseptic Battery System," Stryker (2006) pp. 1-2.

* cited by examiner

STERILE BATTERY CONTAINMENT

BACKGROUND

Many medical devices require a power source to function properly. In some cases, medical devices may be plugged into a wall outlet to receive power. However, tethering a medical device to a wall outlet may be cumbersome or difficult to maneuver for the user. In other scenarios, medical devices may be connected to an intermediate power supply or other piece of capital equipment located between the medical device and a wall outlet. Using such an intermediate power source may also be cumbersome and difficult. Furthermore, in many situations, such medical devices must remain sterile; otherwise a patient may be susceptible to infection or other contamination from being exposed to a non-sterile device. Battery packs could be used with such medical devices. However, such battery packs may be non-sterile. Thus, using a battery could pose increased risks to a patient. In the event that a non-sterile battery is used, the non-sterile medical device may ultimately become exposed to the battery, which may compromise the sterility of the medical device for use with a patient. In short, using a non-sterile power source with a sterile medical device may pose a variety of risks.

Merely exemplary devices that rely on electrical power are disclosed in U.S. Pat. No. 6,500,176, entitled "Electrosurgical Systems and Techniques for Sealing Tissue," issued Dec. 31, 2002; U.S. Pat. No. 7,416,101, entitled "Motor-Driven Surgical Cutting and Fastening Instrument with Loading Force Feedback," issued Aug. 26, 2008; U.S. Pat. No. 7,738,971, entitled "Post-Sterilization Programming of Surgical Instruments," issued Jun. 15, 2010; U.S. Pub. No. 2009/0209990, entitled "Motorized Surgical Cutting and Fastening Instrument Having Handle Based Power Source," published Aug. 20, 2009, now U.S. Pat. No. 8,657,174, issued Feb. 25, 2014; U.S. Pub. No. 2006/0079874, entitled "Tissue Pad for Use with an Ultrasonic Surgical Instrument," published Apr. 13, 2006; U.S. Pub. No. 2007/0191713, entitled "Ultrasonic Device for Cutting and Coagulating," published Apr. 16, 2007; U.S. Pub. No. 2007/0282333, entitled "Ultrasonic Waveguide and Blade," published Dec. 6, 2007; U.S. Pub. No. 2008/0200940, entitled "Ultrasonic Device for Cutting and Coagulating," published Aug. 21, 2008. The disclosure of each of the above-cited U.S. patents and U.S. patent application Publications is incorporated by reference herein.

While several systems and methods have been made for use with an electrically powered medical device, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
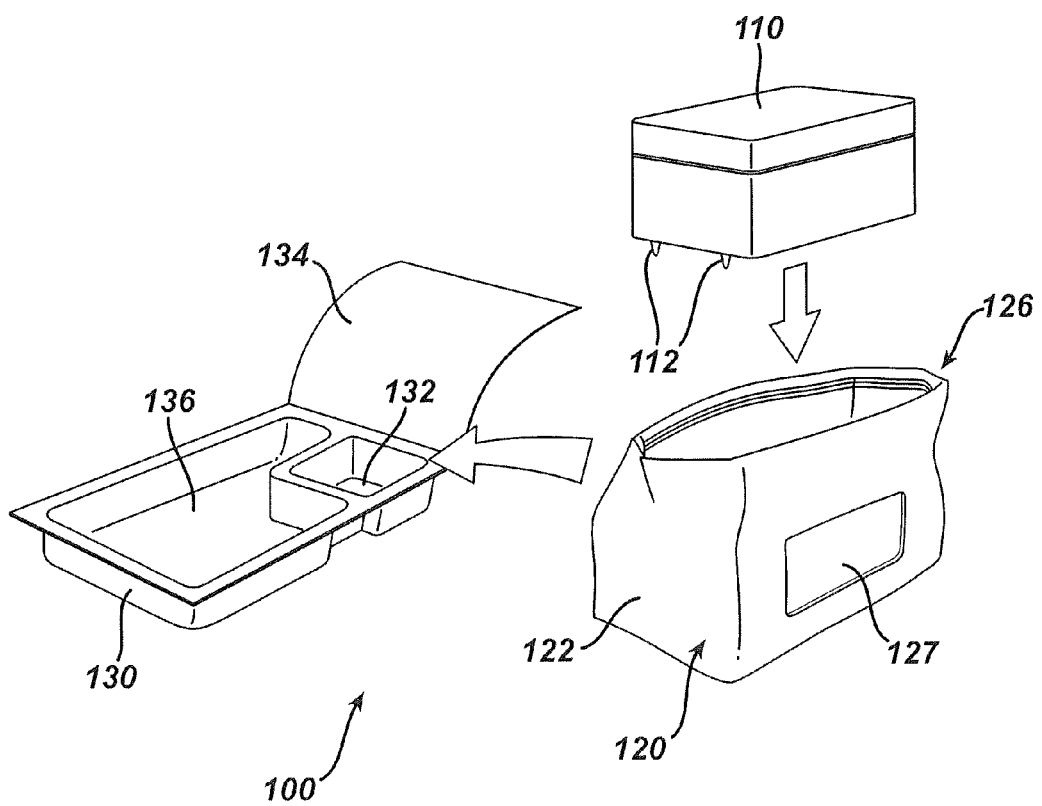
FIG. 1 depicts a perspective view of an exemplary sterilized medical device system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which were filed on Jun. 2, 2011 and the disclosures of all of which are incorporated by reference herein: U.S. patent application Ser. No. 13/151,471, entitled "Medical Device Packaging with Charging Interface," now U.S. Pat. No. 9,000,720, issued Apr. 7, 2015; U.S. patent application Ser. No. 13/151,481, entitled "Motor Driven Electrosurgical Device with Mechanical and Electrical Feedback," now U.S. Pat. No. 9,161,803, issued Oct. 20, 2015; U.S. patent application Ser. No. 13/151,488, entitled "Packaging for Reclaimable Component of a Medical Device," now U.S. Pat. Pub. No. 2012/0111591, published May 10, 2012; U.S. patent application Ser. No. 13/151,498, entitled "Sterile Housing for Non-Sterile Medical Device Component," now U.S. Pat. No. 9,017,851, issued Apr. 28, 2015; U.S. patent application Ser. No. 13/151,503, entitled "Sterile Medical Instrument Charging Device," now U.S. Pat. Pub. No. 2012/0116380, published May 10, 2012; U.S. patent application Ser. No. 13/151,509, entitled "Medical Device Packaging with Window for Insertion of Reusable Component," now U.S. Pat. No. 9,089,338, issued Jul. 28, 2015; U.S. patent application Ser. No. 13/151,512, entitled "Medical Device with Feature for Sterile Acceptance of Non-Sterile Reusable Component," now U.S. Pat. No. 9,072,523, issued Jul. 7, 2015; and U.S. patent application Ser. No. 13/151,515, entitled "Sterile Package System for Medical Device," now U.S. Pat. Pub. No. 2012/0305427, published Dec. 6, 2012. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

FIG. 1 shows an exemplary version of a sterilized medical device system (100) comprising a tray (130), a bag assembly (120), and a battery (110). In general, battery (110) is placed within bag assembly (120), which is then placed within tray (130). Tray (130) is generally sterile such that tray (130) can store an electrically powered medical device (not shown). For example, it will be appreciated that devices such as those shown in U.S. Pat. No. 6,500,176, U.S. Pat. No. 7,416,101, U.S. Pat. No. 7,738,971, U.S. Pub. No. 2009/0209990, now U.S. Pat. No. 8,657,174, U.S. Pub. No. 2006/0079874, U.S. Pub. No. 2007/0191713, U.S. Pub. No. 2007/0282333, and U.S. Pub. No. 2008/0200940 may be modified to run on battery power, and may thus be used with sterilized medical device system (100). In the event that the electrically powered medical device is and must remain sterile, bag assembly (120) will prevent direct physical contact between battery (110) and the electrically powered medical device as it is understood that battery (110) may not always be sterile. Therefore, by using bag assembly (120) to hold battery (110), it will be appreciated that the electrically powered medical device will more likely be protected from contamination, which will be described in further detail below. Furthermore, it will be appreciated that using sterilized medical device system (100) also may allow a medical device to be shipped with battery (110) without connecting battery (110) to the medical device to avoid undesirably draining charge from battery (110) prior to use. As a result, sufficient charge will remain in battery (110) until battery (110) is ready for use with the medical device.

Tray (130) comprises a battery compartment (132) and cover (134). Battery compartment (132) may be sized to fit bag assembly (120) with battery (110) contained within bag assembly (120). Alternatively, battery compartment (132) may be sized to fit compartment assembly (200), described further below. As apparent from FIG. 1, in some versions, battery (110) is placed vertically into bag assembly (120). Then bag assembly (120) is placed into battery compartment (132). It will be appreciated that battery (110) could be inserted into bag assembly (120) in other ways. For example, bag assembly (120) could comprise a side opening or bottom opening to receive battery (110) or any other sort of battery (110) receiving configuration as would be apparent to one of ordinary skill in the art in view of the teachings herein. It will further be appreciated that battery compartment (132) may be used to hold components other than battery (110) or bag assembly (120) containing battery (110). For example, battery compartment (132) may hold components such as PCB boards, control modules, connectors, switches, cables, and/or any other suitable components as would be apparent to one of ordinary skill in the art in view of the teachings herein. Tray (130) further comprises a device compartment (136), which may be used to fit a medical device for use with battery (110). Device compartment (136) and battery compartment (132) comprise molded recesses in tray (130); however, other constructions of tray (130) are contemplated. For example, device compartment (136) and battery compartment (132) may comprise two separate compartments that are bound together. Alternatively, device compartment (136) and battery compartment (132) could be stored in a pouch and transported separately for later use. Other suitable configurations for battery compartment (132) and device compartment (136) will be apparent to one of ordinary skill in the art in view of the teachings herein.

Once battery (110) is placed into battery compartment (132), a medical device such as those, for example, in U.S. Pat. No. 6,500,176, U.S. Pat. No. 7,416,101, U.S. Pat. No. 7,738,971, U.S. Pub. No. 2009/0209990, now U.S. Pat. No. 8,657,174, U.S. Pub. No. 2006/0079874, U.S. Pub. No. 2007/0191713, U.S. Pub. No. 2007/0282333, and U.S. Pub. No. 2008/0200940, may also be placed into tray (130) into device compartment (136). After the desired components are placed into tray (130), tray (130) may be closed and sealed with cover (134). It should be understood that cover (134) could be sealed against tray (130) in a variety of ways. For example, the outer edges of cover (134) could comprise an adhesive for adhering cover (134) against tray (130) to form an airtight seal. Other ways of sealing cover (134) against tray (130) will be apparent to one of ordinary skill in the art in view of the teachings herein. Once sealed, tray (130) with the included medical device and bag assembly (120) could then be shipped, stored, or otherwise prepared for use, which will be described in further detail below. It should be understood that at least some of the contents of tray (130) may be sterilized before they are put in tray (130), such as by using gamma radiation, electron beam radiation, etc. In addition or in the alternative, at least some of the contents of tray (130) may be sterilized after they are put in tray (130), such as by using gamma radiation, electron beam radiation, etc.

Battery (110), as shown in FIG. 1 has a generally rectangular shape, though of course battery (110) may have any other suitable shape. Battery (110) may comprise a lithium ion battery (e.g., prismatic cell type of lithium ion battery, etc.), an alkaline battery, nickel-cadmium, nickel-metal hydride, carbon zinc, oxyride, rechargeable alkaline, or any other suitable battery as will be apparent to one of ordinary skill in the art in view of the teachings herein. In the exemplary version, battery (110) comprises a pair of prongs (112) extending from the bottom of battery (110). Each prong (112) has a spike-like shape extending downward from battery (110). Prongs (112) are able to pierce through bag assembly (120) to electrically connect battery (110) with a medical device, for example, in ways such as those described in U.S. patent application Ser. No. 13/151,498, entitled "Sterile Housing for Non-Sterile Medical Device Component", now U.S. Pat. No. 9,017,851, issued Apr. 28, 2015, the disclosure of which is hereby incorporated by reference. It should therefore be understood that prongs (112) are electrically conductive in the present example. It should also be understood that prongs (112) may include removable caps if desired. Such caps could be blunt to reduce the likelihood that prongs (112) will cause injury or cause puncture of bag assembly (120) until the appropriate time. Alternatively, such caps could be sharp to puncture bag assembly (120), allowing the caps to be removed at the appropriate time after battery (110) has been placed in bag assembly (120). Caps on prongs (112) could also be made of a plastic or other isolating material, substantially reducing the potential for battery (110) to discharge prematurely.

It will be appreciated that rather than prongs (112) being attached to battery (110), prongs (112) could also be attached to the medical device so that battery (110) could be able to receive prongs (112) to establish electrical communication with the medical device to deliver power to the medical device. For instance, battery (110) may include recesses with contacts therein. Such recesses may receive prongs extending from a medical device and battery (110) may then provide power through the contacts and the prongs. In the exemplary version, battery (110) comprises two prongs (112), but it will be appreciated that any suitable number of prongs (112) may be used. Furthermore, rather than prongs (112), other types of connection features may be used. For example, a connecting post, a plurality of electrical contacts, or any other suitable contact as would be apparent to one of ordinary skill in the art in view of the teachings herein may be used.

As shown in FIGS. 1-5, bag assembly (120) comprises an inner bag (124), outer bag (122), side panel (127), and closure feature (126). Bag assembly (120) has a rectangular shape with a narrower top so that bag assembly (120) may store battery (110) and close battery with closure feature (126). While a rectangular shape is shown, any suitable shape for bag assembly (120) may be used as would be apparent to one of ordinary skill in the art in view of the teachings herein. For example, if battery (110) had a cubical or cylindrical shape, then the shape of bag assembly (120) could be accordingly cubical or cylindrical. Additionally, in cases where electrical components other than battery (110) are held by bag assembly (120), bag assembly (120) may be appropriately shaped and sized to fit such components. While the exemplary version shows a satchel-like configuration for bag assembly (120), it will be appreciated that bag assembly (120) may comprise a variety of structures. For example, bag assembly (120) may comprise a rigid box-like structure or any other suitable structure as would be apparent to one of ordinary skill in the art in view of the teachings herein.

Figure 4:
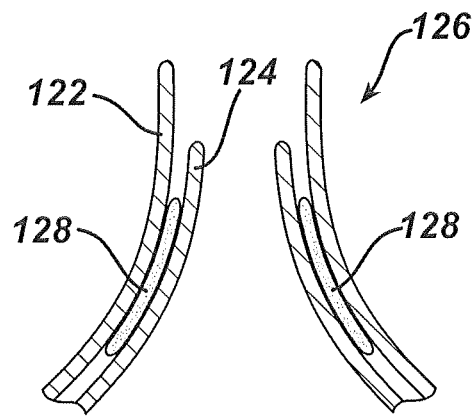
FIG. 4 depicts a side, cross sectional view of a closure feature of the bag of FIG. 2.

Bag assembly (120) of the present example comprises a dual-bag configuration, which is achieved by positioning inner bag (124) within outer bag (122). Inner bag (124) and outer bag (122) have roughly similar shapes and sizes with inner bag (124) having a slightly smaller size such that inner bag (124) can fit within outer bag (122). As seen in FIG. 4, a sterile adhesive (128) is placed between inner bag (124) and outer bag (122), which maintains sterility between inner bag (124) and outer bag (122). Furthermore, sterile adhesive (128) gently adheres inner bag (124) to outer bag (122) such that when inner bag (124) is positioned within outer bag (122), inner bag (124) may be supported by outer bag (122) without collapsing. In some versions, sterile adhesive (128) need not be adherent in the sense that it provides strong structural support. Instead, sterile adhesive (128) may comprise a sterile fluid or gel such that the liquid tension gently holds inner bag (124) and outer bag (122) together. In yet other versions, a sterile fluid may be used between inner bag (124) and outer bag (122) such that the sterile fluid only functions to maintain sterility between inner bag (124) and outer bag (122). Other aspects of sterile adhesive (128) may be used as would be apparent to one of ordinary skill in the art in view of the teachings herein. Furthermore, sterile adhesive (128) may be applied uniformly along the entire outer surface of inner bag (124), along an entire outer perimeter of inner bag (124) but not the entire outer surface of inner bag (124), only in discrete areas along the outer surface of inner bag (124), or in any other suitable fashion. In yet other versions, sterile adhesive (128) may be applied to the inner surface of outer bag (122) prior to positioning inner bag (124) within outer bag (122).

In yet other versions, sterile adhesive (128) could be applied in discrete amounts with non-adherent sheets covering sterile adhesive (128), such that inner bag (124) could be placed within outer bag (122). Thereafter, a user could pull away non-adherent sheets to expose sterile adhesive (128) to adhere inner bag (124) to outer bag (122). Furthermore, as shown in FIG. 4, sterile adhesive (128) may be positioned primarily near to closure feature (126), which will allow the outer surface of inner bag (124) and the inner surface of outer bag (122) to remain sterile even if battery (110), which could be non-sterile, is placed in inner bag (124). Other suitable ways of applying sterile adhesive (128) will be apparent to one of ordinary skill in the art in view of the teachings herein. As a result of sterile adhesive (128) between inner bag (124) and outer bag (122), it will be appreciated that the outer surface of inner bag (124) and the inner surface of outer bag (122) will remain sterile. Additionally, any space between inner bag (124) and outer bag (122) will remain sterile as well.

Figure 2:
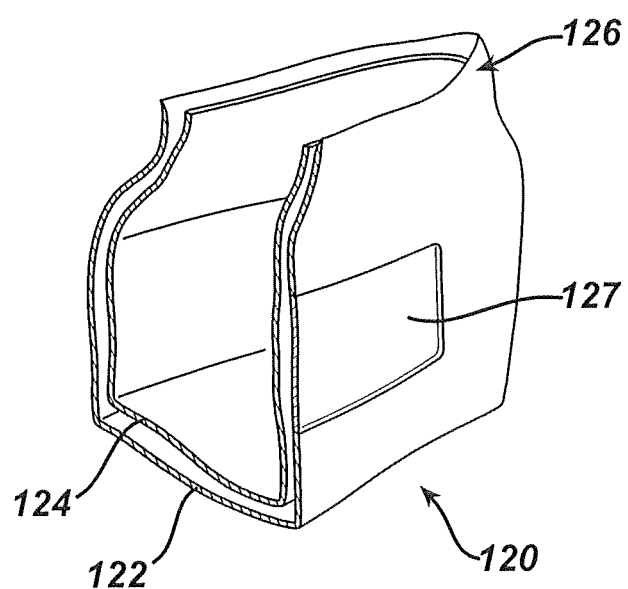
FIG. 2 depicts a perspective, cross sectional view of the bag of the sterilized medical device system of FIG. 1.
Figure 5:
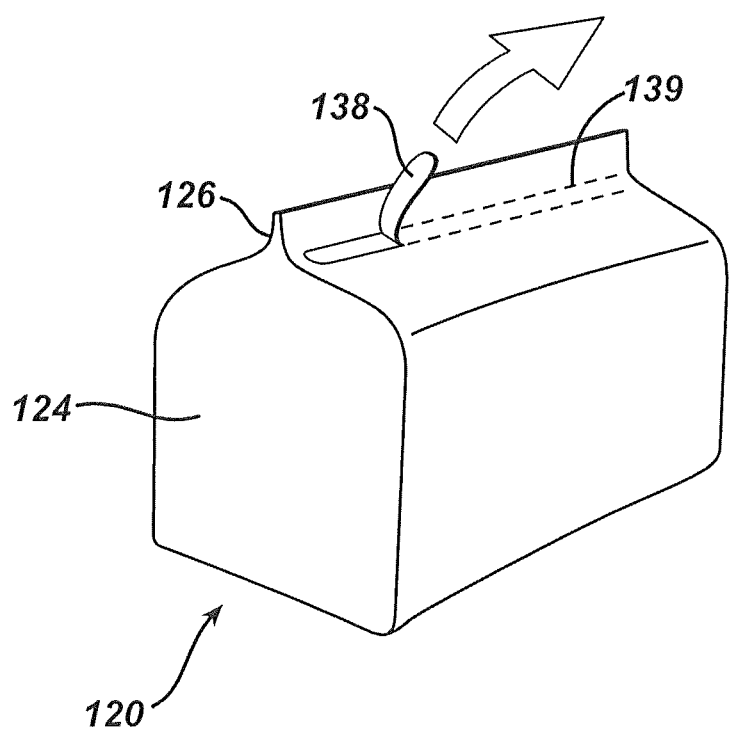
FIG. 5 depicts a perspective view of the bag of the sterilized medical device system of FIG. 1, showing an opening feature of the bag.

Side panel (127), as shown in FIGS. 1, 2, and 5 is configured to inform a user the orientation of battery (110). For example, side panel (127) could convey information such as the location of positive and negative posts of battery (110). Side panel (127) may comprise a graphic or textually conveyed information, or side panel (127) may comprise a transparent, partially transparent, or translucent window. In the exemplary version, side panel (127) has a rectangular shape formed in the wall of outer bag (122). However, it will be appreciated that other shapes for side panel (127) may be used as well. For example, side panel (127) may encompass an entire side of outer bag (122), or side panel (127) may simply comprise any suitable size smaller than an entire side of outer bag (122) to determine positioning and/or orientation of battery (110) within bag assembly (120). In the event that side panel (127) comprises a transparent, partially transparent, or translucent material, it will be appreciated that inner bag (124) may also comprise a similarly constructed window such that a user could view battery (110) within bag assembly (120). If side panel (127) comprises a graphic, then such a graphic may comprise a picture of battery (110) indicating the orientation of battery (110). Additionally, the graphic could comprise a symbol such as a "+" symbol or other abstract representation indicating the location of a positive post of battery (110). Side panel (127) could further comprise textual information that explains to a user the orientation of battery (110) within bag assembly (120). Other suitable variations for side panel (127) will be apparent to one of ordinary skill in the art in view of the teachings herein.

Figure 3:
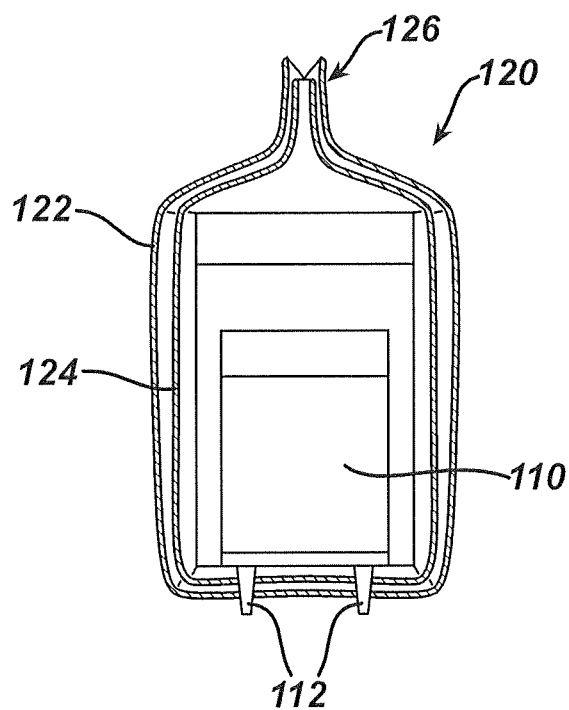
FIG. 3 depicts a side, cross sectional view of the bag of FIG. 2 with a battery.

Closure feature (126) of the present example, as shown in FIGS. 3-4, is able to close outer bag (122) and seal inner bag (124) within outer bag (122), such that contact of outer bag (122) with non-sterile objects or areas will not compromise sterility of inner bag (124). Closure feature (126) may comprise a reclosable seal such as a reclosable zipper seal or slider seal. Thus, bag assembly (120) can be sealed or opened later in the event that inner bag (124) needs to be accessed within outer bag (122). In some other versions, closure feature (126) may comprise a one-way closure feature (e.g., adhesive material, etc.). For example, the one-way closure feature may comprise an adhesive lining the closure feature such that once closure feature (126) closes, it cannot be re-opened without destroying outer bag (122). Furthermore, rather than a reclosable seal, closure feature (126) may comprise a pressure sensitive adhesive strip such that once battery (110) or other relevant components are placed in bag assembly (120), closure feature (126) may be pressed together to seal bag assembly (120). Other ways of sealing bag assembly (120) will be apparent to one of ordinary skill in the art in view of the teachings herein.

To the extent that closure feature (126) allows outer bag (122) to be re-opened for access to inner bag (124), inner bag (124) may also provide some degree of access to the contents of inner bag (124). In the present example, inner bag (124) is closed by a one-way closure feature that comprises an adhesive, such that once inner bag (124) is closed, it cannot be re-opened without destroying inner bag (124). Of course, inner bag (124) may instead have a redo sable seal if desired. Referring back to the present example as shown in FIG. 5, inner bag (124) includes an opening feature (138) that provides one-time opening of inner bag (124) after inner bag (124) has been sealed closed. Opening feature (138) of this example comprises a pull tab embedded into outer bag (122). Opening feature (138) is attached to a resilient strip (139), which is bounded by perforations formed through inner bag (124). Thus, when opening feature (138) is pulled by a user, resilient strip (139) tears out of inner bag (124) thereby creating an opening in inner bag (124) from which battery (110) may be removed. While the exemplary version shows opening feature (138) as providing a pull tab, other alternative versions of opening feature may be used as would be apparent to one of ordinary skill in the art in view of the teachings herein.

In some alternative versions, opening feature (138) may comprise a reclosable seal. Additionally, opening feature (138) may comprise a tamper evident seal such that a user could readily determine whether opening feature (138) has already been engaged to open inner bag (124). Other suitable variations of opening feature (138) will be apparent to one of ordinary skill in the art in view of the teachings herein. It should also be understood that outer bag (122) may include an opening feature (138) as described above, if desired, in addition to or in lieu of inner bag (124) having an opening feature (138).

Having described the general feature of sterilized medical device system (100), an exemplary way of using sterilized medical device system (100) will be described. Battery (110), which may be in some cases non-sterile, may be placed into bag assembly (120). It will be appreciated that the outer surface of inner bag (124) will remain sterile despite a potentially non-sterile battery (110) being placed into inner bag (124). Once battery (110) or possibly other electronic components are placed into bag assembly (120) and sealed using closure feature (126), battery (110) may be charged through the bag using, for example, inductive charging. Thus, battery (110) will become charged without compromising the sterility of the outer surface of inner bag (124). However, battery (110) need not necessarily be charged in the event that a fully charged battery (110) is placed in bag assembly (120). Alternatively, battery (110) may also be charged after being shipped through inductive charging (or using any other suitable techniques), as will be described below.

After sealing bag assembly (120), bag assembly (120) may then be placed into battery compartment (132) of tray (130) along with other relevant medical devices, which will be placed into device compartment (136). Cover (134) may then be sealed such that tray (130) can be shipped or stored until ready to use. Once ready, a user can access device compartment (136) and battery compartment (132) by removing cover (134) in a sterile manner such that sterility of any medical devices in tray (130) is not compromised. The medical device can be removed from tray (130) for handling by a user having sterile hands. Bag assembly (120) may be removed, and if necessary, inductive charging may be used through inner bag (124) and outer bag (122) to charge battery (110). As another merely illustrative example, in versions where prongs (112) protrude through bag assembly (120), battery (110) may be charged through contact with prongs (112).

When desired, inner bag (124) may be removed from outer bag (122) by a user having sterile hands by engaging opening feature (138). Since the outer surface of inner bag (124) maintains sterility, with inner bag (124) still enclosing battery (110), battery (110) may be connected to the medical device to power the medical device without compromising sterility of the medical device. For instance, prongs (112) may be used to electrically connect battery (110) with the medical device through inner bag (124). Once battery (110) and the medical device are connected, the user may then use the medical device for the desired medical procedure. After the medical procedure is over or use of the medical device is complete, inner bag (124) containing battery (110) may be placed back into outer bag (122) to recharge battery (110) using inductive charging (or other techniques) to prepare for the next use.

Figure 6:
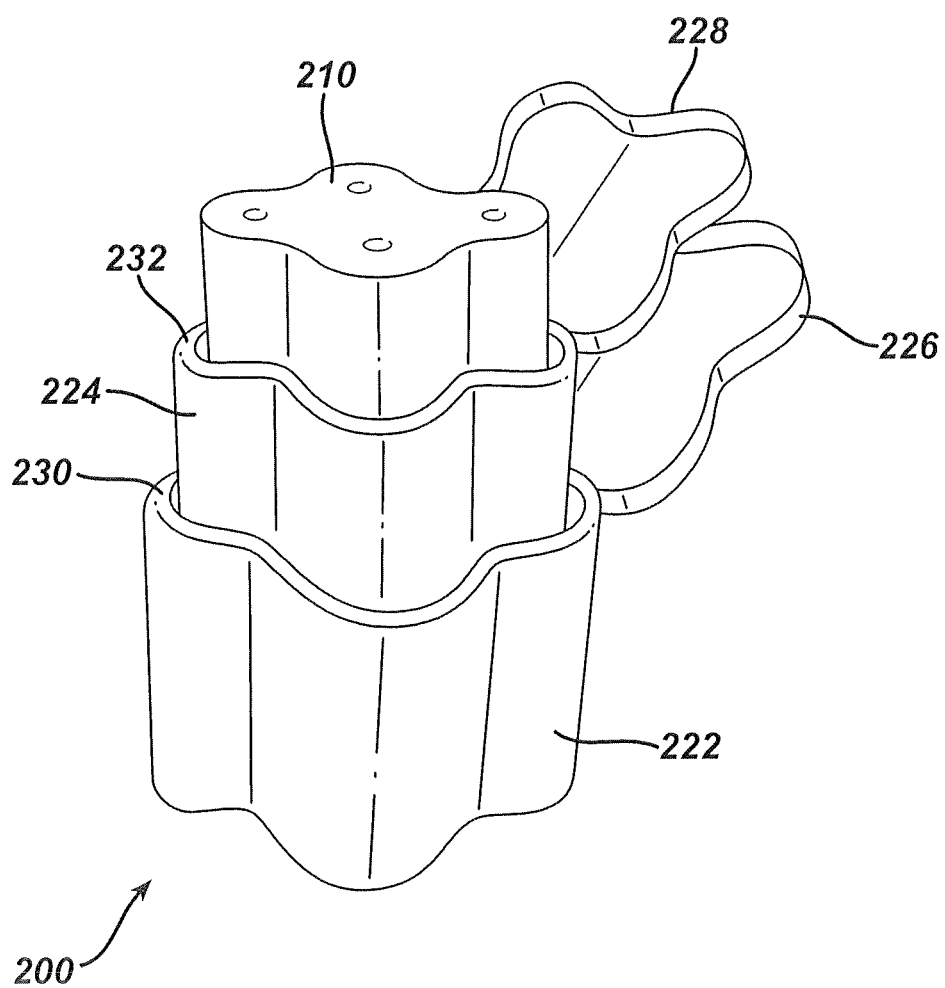
FIG. 6 depicts a perspective view of an exemplary alternative version of a sterilized medical device system having fitted compartments.
Figure 7:
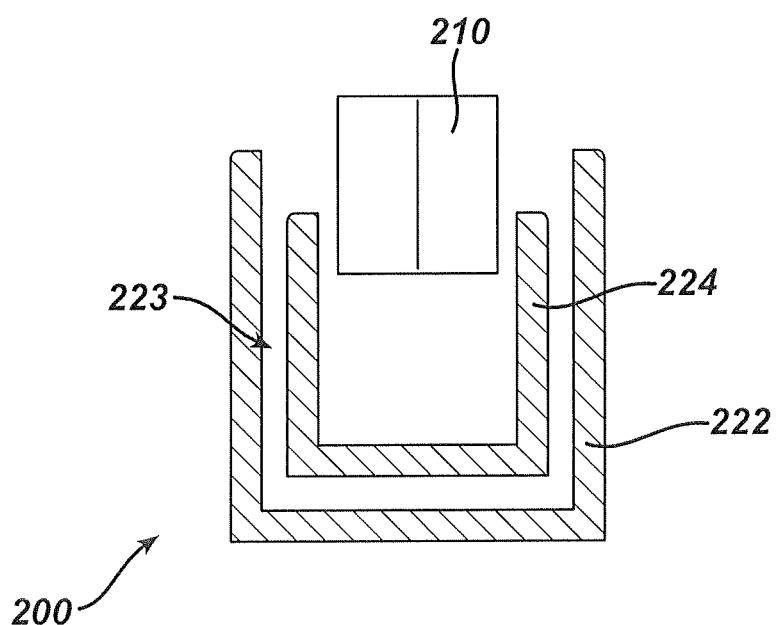
FIG. 7 depicts a side, cross sectional view of the sterilized medical device system of FIG. 6, showing the sterilized layer between the compartments.

It will be appreciated that rather than using bag assembly (120) as shown in FIGS. 1-5, a compartment system (200) may be used as shown in FIGS. 6-7. Of course, other variations will be apparent to one of ordinary skill in the art in view of the teachings herein. Compartment system (200) of the present example comprises an inner compartment (224) and an outer compartment (222). Inner compartment (224) holds a battery pack (210), which comprises a plurality of battery cells held together. In some versions, rather than a plurality of batteries being held together to form battery pack (210), a single cell, or any other suitable configuration may be used as would be apparent to one of ordinary skill in the art in view of the teachings herein. It will be appreciated that compartment system (200) will work similarly to bag assembly (120) of FIGS. 1-5.

Inner compartment (224) is sized and shaped to generally complement the size and shape of battery pack (210). Furthermore, outer compartment (222) is sized and shaped to generally complement the size and shape of inner compartment (224). Thus, battery pack (210) is able to fit within inner compartment (224), which is able to fit within outer compartment (222).

Each of outer compartment (222) and inner compartment (224) further comprises an outer lid (226) and an inner lid (228), respectively. Outer lid (226) forms a fluid-tight seal with an outer lip (230) of outer compartment (222). The fluid-tight seal could be formed using a sealing adhesive or sealing gel or any other suitable sealing means as would be apparent to one of ordinary skill in the art in view of the teachings herein. Inner lid (228) and an inner lip (232) may be similarly sealed to create a fluid tight seal between inner lid (228) and inner compartment (224).

Inner lid (228) may connect to inner compartment (224) through, for example, a living hinge. In other versions, rather than being connected through a living hinge, inner lid (228) and inner compartment (224) need not necessarily be connected. Instead, inner lid (228) may comprise a separate cap member that is configured to form a seal once placed on inner compartment (224). Other ways of connecting inner lid (228) and inner compartment (224) will be apparent to one of ordinary skill in the art in view of the teachings herein. Outer lid (226) and outer compartment (222) may also be connected through, for example, a living hinge. However, it will be appreciated that other suitable ways of connecting outer lid (226) and outer compartment (222) may be used as would be apparent to one of ordinary skill in the art in view of the teachings herein.

As can be seen in FIG. 7, in which lids (226, 228) are omitted for clarity, inner compartment (224) and outer compartment (222) define a sterile region (223) between inner compartment (224) and outer compartment (222). Thus, it will be appreciated that the outer surface of inner compartment (224) will remain generally sterile even if the outer surface of outer compartment (222) is non-sterile. As a result, compartment system (200) may be transported similarly to bag assembly (120) shown in FIGS. 1-5. Thus, once compartment system (200) is transported, a sterile set of hands can remove inner compartment (224) from outer compartment (222) to place inner compartment (224), which contains battery pack (210), into a medical device for use. Due to sterile region (223), sterility of inner compartment (224) will be maintained, which allows battery pack (210) to deliver electrical power to the medical device without compromising the sterility of the medical device. It will further be appreciated that electrical power may be delivered from battery pack (210) to the medical device through the wall of inner compartment (224) by, for example, inductive or capacitive coupling, as shown in application Ser. No. 13/151,471 entitled "Medical Device Packaging with Charging Interface," now U.S. Pat. No. 9,000,720, issued Apr. 7, 2015 the disclosure of which is hereby incorporated by reference.

In some other exemplary versions, prongs connected to battery pack (210) may be used to puncture bottom of inner compartment (224) to establish electrical coupling between battery pack (210) and the medical device, or otherwise provide power through inner compartment (224), without compromising sterility of the medical device when battery pack (210) is connected to the medical device. For example, ways of puncturing the bottom of inner compartment (224) with prongs to establish electrical communication, as well as other ways to provide power through a compartment, are shown in application Ser. No. 13/151,498, entitled, "Sterile Housing for Non-Sterile Medical Device Component," now U.S. Pat. No. 9,017,851, issued Apr. 28, 2015, the disclosure of which is hereby incorporated by reference. Still other suitable ways of delivering electrical power from battery (210) will be apparent to one of ordinary skill in the art in view of the teachings herein.

Of course, battery (210) may be removed from inner compartment (224) and then be inserted into or otherwise coupled with a medical device to provide power to the medical device, without such power also being provided through inner compartment (224). For instance, at the beginning of a procedure, inner compartment (224) may be removed from outer compartment (222), and battery (210) may be removed from inner compartment (224). Battery (210) may then be inserted into or otherwise coupled with a medical device to provide power to the medical device during a medical procedure. At the end of the medical procedure, battery (210) may be removed from the medical device. Battery (210) (and possibly other electrical components) may be dropped back into inner compartment (224). At this stage, battery (210) and the interior of inner compartment (224) may be non-sterile. A user with sterile hands may then use lid (228) to close inner compartment (224), then drop closed inner compartment (224) into outer compartment (222). At this stage, the exterior of inner compartment (224) and the interior of outer compartment (222) may still be sterile, despite battery (210) and the interior of inner compartment (224) being non-sterile. A user may then use lid (226) to close outer compartment (222). The exterior of outer compartment (222) may be non-sterile at this stage. While fully enclosed, battery (210) may be recharged through compartment system (200), such as using inductive charging techniques, mating contacts, and/or using any other suitable structures or techniques. With battery (210) recharged, at the beginning of the next procedure, a user may re-open outer compartment (222) and dump closed inner compartment (224) onto a sterile table. In versions where power may be communicated through inner compartment, a person with sterile hands may insert inner compartment (224) into a medical device or otherwise couple inner compartment (224) with the medical device to provide power to the medical device. Alternatively, a person may open inner compartment (224) to retrieve battery (210) and insert battery (210) into the medical device for use. Still other suitable ways in which compartment system (200) may be used will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a battery pack, wherein the battery pack is operable to deliver electrical power to an electrically powered medical device;
   (b) a first compartment, wherein the first compartment is configured to contain the battery pack, wherein the battery pack is operable to deliver electrical power to the electrically powered medical device while the battery pack is positioned in the first compartment, wherein the first compartment further comprises a closing feature operable to fluidly seal the first compartment, wherein the first compartment and the battery pack are configured to selectively couple with the electrically powered medical device;

(c) a second compartment, wherein the second compartment is configured to contain the first compartment, wherein the first compartment is removable from the second compartment, wherein the first compartment and the second compartment define a sterile area therebetween;

(d) an opening feature in communication with the first compartment, wherein the opening feature comprises a pull tab configured to expose the battery pack from the first compartment when the pull tab is pulled relative to the first compartment and (e) a sterile adhesive positioned in the sterile area, wherein the sterile adhesive is in contact with the first compartment and the second compartment;

wherein each of the first compartment and the second compartment comprises a bag.

2. The apparatus of claim 1, wherein the battery pack further comprises at least one prong operable to establish electrical communication with the electrically powered medical device.

3. The apparatus of claim 2, wherein the at least one prong has a spike shape configured to protrude through the first compartment.

4. The apparatus of claim 1, wherein the closing feature comprises a reclosable seal.

5. The apparatus of claim 1, wherein the closing feature comprises a one-way closure feature.

6. The apparatus of claim 1, wherein the battery pack comprises a rechargeable battery pack, wherein the rechargeable battery pack is configured to be recharged through the first compartment and the second compartment through inductive charging.

7. The apparatus of claim 1, wherein the second compartment comprises a graphical element, wherein the graphical element is configured to convey the orientation of the battery pack within the first compartment.

8. The apparatus of claim 7, wherein the graphical element comprises a translucent window extending through the second compartment, wherein the translucent window extends further through the first compartment.

9. The apparatus of claim 1, wherein the first compartment and the second compartment are similarly shaped.

10. The apparatus of claim 1, further comprising a sterilized tray, wherein the second compartment is positioned within the sterilized tray.

11. An apparatus comprising:
(a) a tray, wherein the tray comprises a first recess and a second recess, wherein the first recess is configured to contain a medical device;
(b) a cover, wherein the cover is configured to fluidly seal the tray;
(c) a battery compartment comprising at least two nested compartments, wherein the at least two nested components comprise an inner compartment and an outer compartment, wherein the battery compartment further comprises a battery contained within the at least two nested compartments, wherein the battery compartment is operable to fit in the second recess when not attached to the medical device, wherein the at least two nested compartments define a sterile space therein, wherein a sterile adhesive is positioned within the sterile area, wherein the sterile adhesive is in contact with the inner compartment and the outer compartment, wherein the battery compartment is configured to couple with the medical device, wherein the battery is operable to deliver electrical power to the medical device, wherein the battery compartment further comprises an opening feature, wherein the opening feature comprises a pull tab attached to a strip coupled to the inner compartment, wherein the strip is configured to tear the inner compartment in response to pulling on the tab.

12. The apparatus of claim 11, wherein the battery compartment further comprises visual indicia, wherein the visual indicia is operable to indicate the orientation of the battery.

13. The apparatus of claim 11, wherein the battery compartment comprises a closing feature.

14. An apparatus comprising:
(a) a battery pack, wherein the battery pack is operable to deliver electrical power to an electrically powered medical device;
(b) a first compartment, wherein the first compartment is configured to contain the battery pack, wherein the battery pack is operable to deliver electrical power to the electrically powered medical device while the battery pack is positioned in the first compartment, wherein the first compartment further comprises a closing feature operable to fluidly seal the first compartment, wherein the first compartment and the battery pack are configured to selectively couple with the electrically powered medical device; and
(c) a second compartment, wherein the second compartment is configured to contain the first compartment, wherein the first compartment is removable from the second compartment, wherein the first compartment and the second compartment define a sterile area therebetween, wherein a sterile adhesive is positioned within the sterile area, wherein the sterile adhesive is in contact with the first compartment and the second compartment;

wherein at least one of the first compartment and the second compartment comprises a fitted compartment molded to fit the battery pack.

15. The apparatus of claim 14, further comprising a sterilized tray, wherein the second compartment is positioned within the sterilized tray.

16. The apparatus of claim 14, wherein the first compartment and the second compartment are identically shaped.

17. The apparatus of claim 14, wherein the first compartment comprises a compartment portion and a lid portion, wherein the compartment portion and the lid portion are connected by a living hinge.

* * * * *